United States Patent [19]

Krzysik

[11] Patent Number: 4,973,476

[45] Date of Patent: Nov. 27, 1990

[54] LEAVE-IN HAIR CONDITIONERS

[75] Inventor: Duane G. Krzysik, Midland, Mich.

[73] Assignee: Dow Corning Corporation, Midland, Mich.

[21] Appl. No.: 452,663

[22] Filed: Dec. 18, 1989

[51] Int. Cl.$^5$ .......................... A61K 7/06; A61K 7/075
[52] U.S. Cl. ........................................ 424/71; 424/47; 424/70
[58] Field of Search ............................ 424/70, 71, 47

[56] References Cited

U.S. PATENT DOCUMENTS

| | | | |
|---|---|---|---|
| 4,387,090 | 6/1983 | Bolich, Jr. .............................. | 424/70 |
| 4,472,375 | 9/1984 | Bolich et al. ........................... | 424/70 |
| 4,563,347 | 1/1986 | Starch ................................... | 424/70 |
| 4,597,962 | 7/1986 | Grollier et al. ........................ | 424/47 |
| 4,749,732 | 6/1988 | Kohl et al. ............................. | 524/43 |

FOREIGN PATENT DOCUMENTS 313714  6/1987  Japan.

Primary Examiner—Merrell C. Cashion, Jr.
Assistant Examiner—Amy Hulina
Attorney, Agent, or Firm—Sharon K. Severance

[57] ABSTRACT

What is disclosed is a hair conditioning composition that is left on the hair after application to the hair (no rinsing required). The composition is comprised of a volatile silicone and a functional silicone. Optional silicone and non-silicone components can also be added to the composition.

11 Claims, No Drawings

LEAVE-IN HAIR CONDITIONERS

This application pertains to leave-in silicone hair conditioners comprised of a volatile cyclic or linear silicone, and at least one functional silicone. The conditioners are applied onto wet or dry hair and the volatile silicone evaporates depositing the functional silicone onto the hair. The silicone leave-in hair conditioners impart to the hair improved wet combing properties as well as conditioning properties.

BACKGROUND OF THE INVENTION

The use of silicones in hair conditioning compositions is known in the art. Typically, the silicones are mixed into the conditioning composition in small quantities with other non-silicone conditioning ingredients. The conditioning composition is typically diluted with water for application to the hair. Following application to the hair the conditioner is rinsed from the hair with water. Over or under rinsing can often result in under or over conditioning, respectively. The most common silicone materials used for conditioning are organopolysiloxanes and amine-functional silicones.

Most conditioners formulated with the amine functional silicones are those that are applied to the hair for several minutes and then rinsed from the hair using water. In the process of rinsing the hair it is possible to remove some of the amine functional silicone, which can result in poor conditioning. Most known conditioners also contain non- silicone materials as required ingredients in the composition. The non-silicone materials are added to provide additional conditioning properties, to provide an easy means for application or to improve wet or dry hair properties.

U.S. Pat. No. 4,597,962 to Grollier et al. teaches a cosmetic composition which contains at least one cationic silicone polymer. The cationic silicone polymers preferred are those known under the name of Amodimethicone. They are present in the at levels of 0.05% to 7%. The cosmetic compositions taught by Grollier are usually in the form of aqueous or aqueous-/alcohol dispersions and can be formulated into numerous types of products. It is preferred to rinse the composition from the hair after several minutes of treatment.

U.S Pat. No. 4,749,732 to Kohl el al. teaches the use of modified aminoalkyl substituted polydiorganosiloxanes in hair care products The modified aminoalkyl substituted polysiloxane is dissolved or dispersed into a carrier at levels from 0.01 to 10 per 50 to 100 parts carrier liquid. Volatile silicones are not taught as suitable carriers and the conditioners are rinsed from the hair after several minutes of treatment. The role of the carrier in the Kohl et al. patent is to dilute the silicone polymer to allow uniform application. The preferred conditioner formulation is an emulsion of the modified aminoalkyl substituted polysiloxane in water.

U.S. Pat. No. 4,563,347 to Starch teaches a composition which contains a silicone that may contain amine functionality. Additional ingredients include surfactants, additives that provide freeze-thaw stability and water. The silicones are present at levels of 1 to 61 percent by weight. It is preferred to use the conditioner treatment after shampooing and they are rinsed from the hair after several minutes of treatment.

The use of cyclomethicone or dimethicone (volatile silicones) in hair conditioning compositions is also known in the art. As with the amine functional silicones, the hair conditioning compositions which contain the volatile silicones are rinsed from the hair after several minutes of treatment and additionally contain non-silicone materials. The known conditioners containing volatile silicones are usually used in water based systems in which water is the delivery means.

U.S. Pat. No. 4,387,090 to Bolich, Jr. teaches a hair condition composition containing a volatile liquid conditioning agent which is thickened with a hydrophobic thickener. The volatile liquid conditioning agents encompass cyclic and linear polydimethylsiloxanes and are present at 1 to 99% by weight. It is preferred to dissolve the composition in water for delivery purposes such that the silicone is only present at levels of 2 to 10 percent by weight. The compositions taught by Bolich, Jr. are rinsed from the hair after several minutes of treatment.

U.S. Pat. No. 4,472,375 to Bolich, Jr. et al. teaches a hair conditioning composition in the form of an emulsion which contains a volatile agent, a thickening agent, a cationic hair conditioning agent and water. Volatile silicones can be useful as the volatile agent when present at levels of 1 to 13 percent by weight. The cationic hair conditioning agents are quarternary amines. Quarternary Amine functional siloxanes are not taught as being useful as the conditioning agent. The conditioners are rinsed from the hair after several minutes of treatment.

Japanese Patent No. 63313714 to Torii, published Dec. 21, 1988, discloses a hair conditioning composition containing a high molecular weight silicone and one or more silicone derivatives such as amine functional, fluoro functional, alkyl functional, dimethyl fluids, phenylmethyl fluids. This composition may be dissolved in a low boiling oil which may be silicone in nature. The high molecular weight silicone is a required ingredient in the composition as taught by Torii.

The novelty of the instant invention is a hair conditioner which can be comprised of only silicone containing components and is not rinsed from the hair after application. It is not necessary to dilute the composition to achieve application to the hair. Because of the method for applying the conditioner, thickening agents which were used in most other conditioners are not desired.

It is an object of this invention to provide a novel hair conditioning compositions comprising a volatile silicone and at least one functional silicone.

It is further an object of this invention to provide a method of conditioning hair using the compositions of the instant invention,

THE INVENTION

The instant invention pertains to a novel hair conditioning composition and a method of conditioning hair using the novel composition.

The hair conditioning composition is comprised of a volatile silicone and at least one functional silicone selected from amine functional silicones, vinyl functional silicones, dimethylpolysiloxane fluids, hydroxyl endblocked polysiloxanes, phenylmethyl polysiloxanes, alkyl substituted polysiloxanes, halogenalkyl functional silicones, and acrylate functional silicones. The composition can further comprise optional ingredients such as fragrances, anti-static agents, colorants, vitamins, herbal extracts and others.

In the instant invention, the hair conditioning composition is applied to the hair, the volatile silicones evaporate from the hair leaving the functional silicone(s) deposited on the hair which then provide the conditioning properties to the hair. There is no need for rinsing the hair conditioning composition of the instant invention from the hair because of the volatile nature of the conditioner. The volatile silicones function as a carrier for the functional silicones, provide detangling benefits, allow for even application to the hair using small quantities of the hair conditioning composition and provide other temporary conditioning benefits.

The volatile silicones useful in the hair conditioners of the instant invention can be linear or cyclic in structure or a combination of both. Cyclic silicones useful are selected from those consisting of the general formula

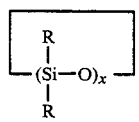  (I)

where each R is independently selected from an alkyl group consisting of 1 to 10 carbon atoms and an aryl group consisting of 6 to 10 carbon atom; and x has the value of 3 to 7. The preferred cyclic silicones of the instant invention are those where R predominantly comprises the group —$CH_3$ and x is 4 or 5 or a mixture thereof.

Linear volatile silicone useful in the conditioning compositions of the instant invention are selected from the group consisting of the general formulas

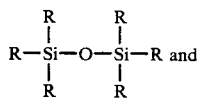  (II)

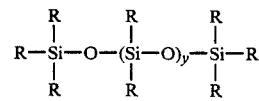  (III)

where R is as described above and y has the value of 1 to 5. The preferred linear volatile silicones are those of formula (II) where R is predominantly the group —$CH_3$.

The volatile silicones useful in the instant invention are commercially available or produced from known methods. Products useful include, but are not limited to, hexamethyldisiloxane. octamethyltrisiloxane. decamethyltetrasiloxane. hexamethylcyclotrisiloxane, octamethylcyclotetrasiloxane, decamethylcyclopentasiloxane, low viscosity trimethyl endblocked polydimethylsiloxanes, cyclomethicone. dimethicone, polydimethyl cyclic siloxanes and mixtures thereof. Preferred volatile silicones include and hexamethyldisiloxane, 0.65 cs trimethyl endblocked polydimethylsiloxanes and polydimethyl cyclic siloxanes with chain lengths (x) of 4 and 5.

It is preferred that the volatile silicone comprise 75 to 99.9 percent by weight of the hair conditioning composition. The more preferred range is 90 to 99.5 percent by weight of the hair conditioning composition.

The functional silicones useful in the hair conditioning composition of the instant invention are selected from amine functional silicones, vinyl functional silicones, dimethyl-polysiloxane fluids, hydroxyl endblocked polysiloxanes, phenylmethyl polysiloxanes, alkyl substituted polysiloxanes. halogenalkyl functional silicones, and acrylate functional silicones and mixtures thereof.

The preferred functional silicones useful in the hair conditioners of the instant invention include, but are not limited to, the following linear and cyclic structures

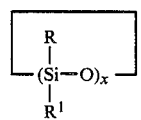  (IV)

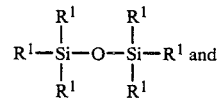  (V)

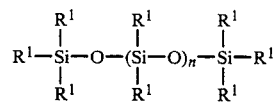  (VI)

where R is as described above; each $R^1$ is independently selected from R and a functional group whereby the functional group is selected from saturated or unsaturated alkyl groups consisting of 1 to 10 carbon atoms, substituted or unsubstituted aryl groups consisting of 6 to 15 carbon atoms, halogenalkyl groups consisting of 1 to 6 carbon atoms, amine functional groups, the group —OH, and acrylate functional groups; n has the value of 1 to 10,000 and x is as described above. It is preferred that the functional group comprise at least 0.1 percent of the total $R^1$ groups on the siloxane.

These various functional silicones may be exemplified by, but not limited to, the following structures

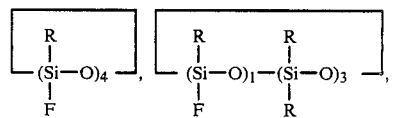

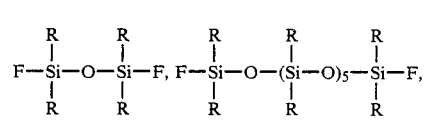

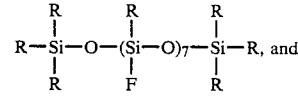

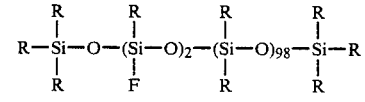

where R is as described above and F is the functional group.

The functional silicones should comprise at least 0.1 percent by weight of the total hair conditioning composition. It is preferred thai each functional silicone individually comprise no more than 5 percent by weight of the total hair conditioning composition and that the sum of the functional silicones comprise no more than 10 percent by weight of the hair conditioning composition.

The functional silicone can be selected from the group comprising amine functional silicones. Almost any amine functional silicone which can be blended into the volatile silicone is useful in the hair conditioning composition of the instant invention. These include primary, secondary and quarternary mono and diamines. They further include acetamides, acrylamides, and other modified amines. The amine functional group may be located on the terminal silicone or the may be located along the backbone such that they comprise random or structured polymers. The remaining $R^1$ groups are selected from R where R is a phenyl group or a lower alkyl group such as methyl or ethyl. The amine functional silicones useful in the instant invention are known in the art or can be prepared from known methods.

The amine functional group may be further exemplified by the general formulas

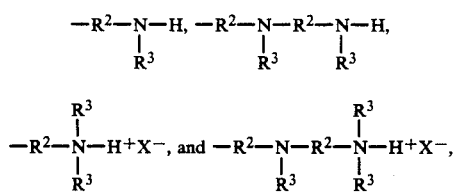

where each $R^2$ is independently selected from an alkylene group consisting of 1 to 10 carbons and an arylene group consisting of 6 to 10 carbons; whereby said $R^2$ group may optionally contain an ether oxygen within the aliphatic segments thereof; each $R^3$ is independently selected from the hydrogen atom, R, the group

where $R^4$ is selected from R, and the groups —CH—CH$_2$, —OH, —R$^2$—OH, and —C(CH$_3$)—CH$_2$; and X is an electronegative group such as a halogen.

The amine functional group can be even further exemplified by the structures

—CH$_2$CH$_2$CH$_2$NH$_2$, —CH$_2$CH(CH$_3$)CH$_2$NH,
$\phantom{-CH_2CH_2CH_2NH_2, -CH_2CH(CH_3)CH_2N}$|
$\phantom{-CH_2CH_2CH_2NH_2, -CH_2CH(CH_3)CH_2NH}$CH$_3$

—CH$_2$CH$_2$CH$_2$NHCH$_2$CH$_2$NH$_2$,

—CH$_2$CH(CH$_3$)CH$_2$NHCH$_2$CH$_2$NH$_2$,

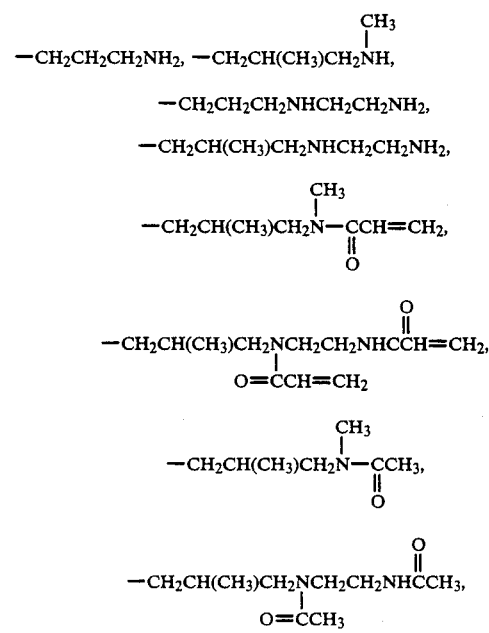

-continued
—CH$_2$CH$_2$CH$_2$NH$_3^+$Cl$^-$, —CH$_2$CH$_2$CH$_2$NHCH$_2$CH$_2$NH$_3^+$Cl$^-$ The functional silicone can further be selected from the group comprised of vinyl functional silicones. The vinyl functional silicones useful in the instant invention are those that contain a vinyl group directly attached to the silicone such that $R^1$ may be H$_2$C=CH— or those that contain a vinyl group terminal on an alkyl chain such that $R^1$ may be H$_2$C=CH—R$^2$— where $R^2$ is as described above. When $R^1$ is not a vinyl functional group, it is preferred that $R^1$ be R where R is the phenyl group or a lower alkyl such as methyl or ethyl. Methods for preparing the vinyl functional silicones are known in the art or they are commercially available.

The functional silicone can further be selected from the groups comprising dimethylpolysiloxane and methylphenyl fluids. The dimethylpolysiloxane fluids, and phenylmethyl fluids useful in the instant invention are those in which all $R^1$ groups are the group R. It is preferable for the dimethyl-polysiloxane fluids that R be predominantly the group —CH$_3$. It is also preferable that the dimethyl polysiloxane fluids be non-volatile. The phenylmethyl fluids are those in which at least 20% of the R groups are phenyl It is preferable that the remaining R groups on the phenylmethyl silicone fluids be lower alkyl groups and more preferably methyl. Again it is preferable that the phenylmethyl silicone fluids be non-volatile.

The functional silicone can further be selected from the group comprising alkyl functional silicones. The alkyl functional silicones are those compounds in which all $R^1$ groups are the R group however, one or more of the R groups should be an alkyl group consisting of 3 or more carbon atoms. The alkyl groups may be linear or branched alkyl groups. The alkyl groups can be exemplified by propyl, iso- propyl, iso-butyl, hexyl, octyl and others.

The functional group can further be selected from the group comprising hydroxyl endblocked polysiloxanes. The hydroxyl endblocked polysiloxanes most useful in the instant invention are those of formula (VI) where $R^1$, the hydroxyl group (—OH), is on the terminal ends of the molecule and the remaining $R^1$ groups are R. The hydroxyl endblocked polysiloxanes can be exemplified by the general formula

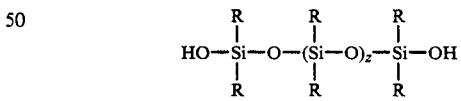

where R is as described above and z has a value such that the molecular weight is greater than 2,000. It is preferred that R be selected from the phenyl group or lower alkyls such as methyl or ethyl.

The functional silicone can further be selected from the group comprising haloalkyl functional siloxanes. When $R^1$ represents the halogenalkyl group, it can be exemplified by the general formula X-R$^2$- where X is a halogen and $R^2$ is as described above. The halogenalkyl group may be further exemplified by chloroalkyl-, bromoalkyl- and fluoroalkyl- groups such as chloromethyl-, trifluoropropyl-, and chloropropyl-. The halogenalkyl groups can be terminal of the silicone or they can be along the silicone polymer backbone. When $R^1$ is not the halogenalkyl group it is preferred than $R^1$ is a lower alkyl such as methyl or ethyl or the group phenyl.

The functional silicone can further be selected from the group comprised of acrylate functional silicones. Of particular usefulness are those silicones containing acryloxy or methacryloxy functional groups where $R^1$ is represented by the group —$R^2$—O—A where $R^2$ is as described above and A is the group

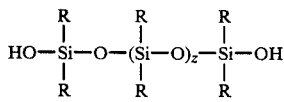

wherein $R^6$ is selected from the hydrogen atom or the group —$CH^3$

The hair conditioning composition can further comprise optional ingredients that are not reactive with the functional group or will not provide adverse effects to the hair if not rinsed from the hair after application. These optional ingredients comprise both silicone and non-silicone containing materials.

Non-silicone optional ingredients include anti-static agents, fragrances, colorants, vitamins, herbal extracts, organic esters, compatibilizers, surfactants and others. These optional ingredients should be present in quantities such that when deposited and left on the hair they do not provide undesired properties to the hair or scalp.

Volatile organics, solvents, alcohols and water can be used as a diluent for the hair conditioning composition. The use of a diluent may aid in application to the hair especially when applying from a spray or aerosol. It is preferred that when the hair conditioning composition is diluted there be at least 10 weight percent of the silicone hair conditioning composition present and more preferably at least 50 weight percent of the hair conditioning composition present in the diluted solution. The diluent should, again, be volatile such that rinsing of the hair is not needed after the application of the hair conditioning composition.

When using water as a diluent it is possible to produce emulsions of the oil in water and water in oil type from the hair conditioning composition and apply the emulsion to the hair without loss in performance from the silicone components.

The preferred composition of this invention is one that contains at least 98 percent by weight of a volatile silicone and 1 to 2 percent of an amine functional silicone and optionally contains 0.1 to 0.2 percent of a hydroxyl endblocked polysiloxane. The preferred hair conditioning composition is easily applied to the hair and does not further require a diluent to ensure even application.

The hair conditioning composition is formulated by blending or mixing together the various silicones and optional ingredients. The hair conditioning composition can be applied to the hair as a liquid, aerosol, spray, mist and others.

The hair conditioning composition can be applied to the hair both wet and dry. The hair conditioner should be worked into the hair by means such as massaging, combing, brushing, and others. It is not necessary to rinse the conditioner from the hair after application. For optimal performance. it is preferred to apply the hair conditioning composition of the instant invention to freshly shampooed hair before drying. After application the hair is dried and styled in the desired manner. It is not necessary to apply large quantities of the conditioner to the hair. Quantities larger than 0.5 grams and more preferably less than 10 grams are sufficient to provide a conditioned effect and ensure even application on the hair.

Upon drying the volatile silicones are evaporated from the hair depositing the functional silicones and any optional ingredients onto the hair. While the volatile silicones are present on the hair, combing of the hair is improved. After drying the hair is left with a conditioned effect. This conditioning effect includes shine, feel, detangling, faster drying time and improved dry combing.

So that those skilled in the art can understand and appreciate the invention taught herein, the following examples are presented, it being understood that these examples should not be used to limit the scope of this invention over the limitation found in the claims attached hereto.

EXAMPLE 1

A conditioner was formulated by mixing 98 weight percent of polydimethyl cyclic siloxanes (where the average chain is 4 to 5) and 2 weight percent of an amine functional silicone of the formula

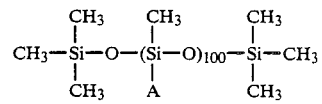

where A is selected from the group —$CH_2CH(CH_3)CH_2NHCH_2CH_2NH_2$ and the group —$CH_3$ such that the siloxane contains 2 mole percent of amine functional group.

The conditioner was applied to human hair that was freshly shampooed. The hair had great combing properties both wet and dry and detangled easily. Upon drying the hair had a conditioned effect with good feel and shine. The hair appeared to dry faster than hair that had not been treated with the conditioner.

EXAMPLE 2

A conditioner was formulated by mixing 97 weight percent of polydimethyl cyclic siloxanes (where the average chain is 4 to 5) with 2 weight percent of the amine functional silicone used in example 1. To that mixture, 1 weight percent of a mixture consisting of 14% hydroxyl endblocked polydimethyl siloxane in polydimethyl cyclic siloxanes (chain length predominantly 4 and 5) was added.

The conditioner was applied to freshly shampooed hair. The application of the conditioner to the hair appeared to be easier than in example 1. Upon drying the hair had a conditioned effect with good feel and shine. Dry feel was better than in example 1.

EXAMPLE 3

A conditioner was formulated by mixing 98 weight percent of polydimethyl cyclic siloxanes (where the average chain is 4 to 5), and 2 weight percent and an amine functional silicone of the formula

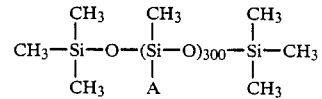

where A is selected from the group —CH$_2$CH(CH$_3$)CH$_2$NHCH$_2$CH$_2$NH$_2$ and the group —CH$_3$ such that the siloxane contains 0.7 mole percent of amine functional group.

The conditioner was applied to freshly shampooed hair. Upon drying the hair had a conditioned effect but lacked body.

EXAMPLE 4

A detangling spray was formulated by mixing 79 weight percent of polydimethyl cyclic siloxanes where the average chain is 4 to 5 with 0.5 weight percent of the amine functional silicone used in example 1. To that mixture, 0.5 weight percent of a mixture consisting of 14% hydroxyl endblocked polydimethyl siloxane in polydimethyl cyclic siloxanes (chain length predominantly 4 and 5) and 20 weight percent 200 proof ethanol was added.

The spray was applied to freshly shampooed hair. The hair detangled well when combed wet. Upon drying the hair had an excellent sheen and felt soft. The spray resulted in a cool feeling on the scalp after application.

EXAMPLE 5

A conditioner was formulated by mixing 98 weight percent of polydimethyl cyclic siloxanes (where the average chain is 4 to 5), and 2 weight percent and a vinyl functional silicone of the formula

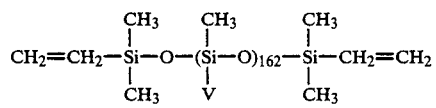

where V is selected from the group —CH$_2$=CH$_2$ and the group —CH$_3$ such that the siloxane contains 23.5 mole percent of vinyl functional group.

The conditioner was applied to freshly shampooed hair. The hair detangled easily upon combing. Upon drying the hair had a great sheen and felt soft.

What is claimed is:

1. A hair conditioning composition comprising
   (i) a volatile silicone present in an amount of from 75–99.9 weight percent of the composition selected from linear and cyclic polysiloxanes;
   (ii) at least one functional silicone present in an amount of from 0.1–10 weight percent of the composition selected from the group having the general formula

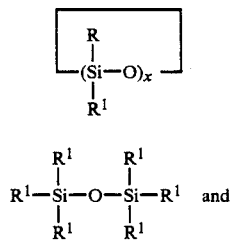

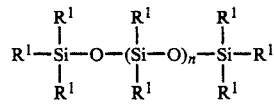

where each R is independently selected from an alkyl group consisting of 1 to 10 carbon atoms and an aryl group consisting of 6 to 10 carbon atom; each R$^1$ is independently selected from R and a functional group whereby the functional group is selected from saturated or unsaturated alkyl groups consisting of 1 to 10 carbon atoms, substituted or unsubstituted aryl groups consisting 6 to 15 carbon atoms, amine functional groups, the group -OH, and acrylate functional groups; x has the value of 3 to 6; and n has the value of 1 to 10,000.

2. A composition as claimed in claim 1 wherein the volatile silicone is a cyclic polysiloxane of the general formula
where each R is independently selected from an alkyl group consisting of 1 to 10 carbon atoms and an aryl group consisting of 6 to 10 carbon atom; and x has the value of 3 to 6.

3. A composition as claimed in claim 2 wherein the cyclic polysiloxane is a mixture of octamethylcyclotetrasiloxane and decamethylcyclopentasiloxane.

4. A composition as claimed in claim 1 wherein the volatile silicone is a linear polysiloxane selected from the group having the general formula

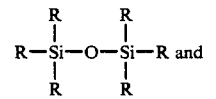

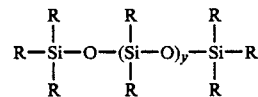

where each R is independently selected from an alkyl group of 1 to 4 carbon atoms and an aryl group consisting of to 10 carbon atom; and y has the value of 1 to 5.

5. A composition as claimed in claim 4 wherein the volatile silicone is hexamethyldisiloxane.

6. A composition as claimed in claim 1 wherein the functional silicone is an amine functional silicone.

7. A composition as claimed in claim 1 wherein the functional silicone comprises an amine functional silicone and a hydroxyl functional silicone.

8. A composition as claimed in claim 1 wherein the functional silicone is a vinyl functional silicone.

9. A method of conditioning hair by
   (A) applying the composition as claimed in claim 1 to the hair; and
   (B) allowing the volatile silicone to evaporate.

10. A method as claimed in claim 9 wherein the composition is applied as a liquid.

11. A method as claimed in claim 9 wherein the composition is applied as a spray.

* * * * *

REEXAMINATION CERTIFICATE (2628th)
United States Patent [19]
Krzysik

[11] B1 4,973,476
[45] Certificate Issued Jul. 18, 1995

[54] LEAVE-IN HAIR CONDITIONERS

[75] Inventor: Duane G. Krzysik, Midland, Mich.

[73] Assignee: Dow Corning Corporation, Midland, Mich.

Reexamination Request:
No. 90/003,161, Aug. 16, 1993

Reexamination Certificate for:
Patent No.: 4,973,476
Issued: Nov. 27, 1990
Appl. No.: 452,663
Filed: Dec. 18, 1989

[51] Int. Cl.[6] .......................... A61K 7/11; A61K 7/06
[52] U.S. Cl. .......................... 424/70.12; 424/70.121; 424/47
[58] Field of Search .................. 424/70, 71, 47, 70.12, 424/70.122

[56] References Cited
U.S. PATENT DOCUMENTS
4,855,129 8/1989 Steinbach .......................... 424/63

OTHER PUBLICATIONS

*Cosmetics and Toiletries,* Charles Todd & Timothy Byers, "Volatile silicone fluids for cosmetic formulation", Jan. 1976.

"Information about Volatile Silicone Fluid—Dow Corning® 244, 245, 344 and 345 Fluids; Dow Corning® 200 Fluid, 0.65 cs", Dow Corning Corporation Form No. 22-904-82, 1982.

"Information about Volatile Silicone Fluid—Dow Corning® Q2-1401 Fluid", Dow Corning Corporation, Form No. 24-405A-87, 1987.

*Primary Examiner*—Thurman K. Page

[57] ABSTRACT

What is disclosed is a hair conditioning composition that is left on the hair after application to the hair (no rinsing required). The composition is comprised of a volatile silicone and a functional silicone. Optional silicone and non-silicone components can also be added to the composition.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, lines 3–11:

The functional silicone can further be selected from the group comprised of acrylate functional silicones. Of particular usefulness are those silicones containing acryloxy or methacryloxy functional groups where $R^1$ is represented by the group —$R^2$—O—A where $R^2$ is as described above and A is the group

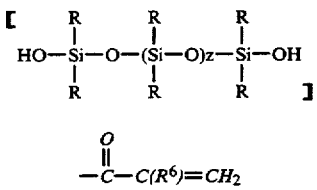

wherein $R^6$ is selected from the hydrogen atom or the group —$CH_3$.

AS A RESULT OF REEXAMINATION, IT HAS BEEN DETERMINED THAT:

Claims 1–11 are cancelled.

New claims 12 and 13 are added and determined to be patentable.

12. *A hair conditioning composition comprising*
   (i) *a volatile silicone present in an amount of from 75–99.9 weight percent of the composition selected from linear and cyclic polysiloxanes;*
   (ii) *at least one functional silicone present in an amount of from 0.1–10 weight percent of the composition selected from the group having the general formula*

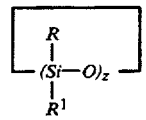

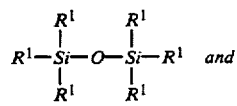

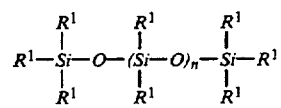

*where each R is independently selected from an alkyl group consisting of 1 to 10 carbon atoms and an aryl group consisting of 6 to 10 carbon atom; each $R^1$ is independently selected from R and a functional group whereby the functional group is selected from saturated or unsaturated alkyl groups consisting of 1 to 10 carbon atoms, substituted or unsubstituted aryl groups consisting 6 to 15 carbon atoms, amine functional groups, the group —OH, and acrylate functional groups; x has the value of 3 to 6; and n has the value of 1 to 10,000; the functional silicone being selected from the group consisting of (a) amine functional silicones, (b) acrylate functional silicones, and (c) a mixture of an amine functional silicone and a hydroxyl functional silicone.*

13. *A method of conditioning hair by applying the composition in claim 12 to hair and allowing the volatile silicone to evaporate.*

* * * * *